United States Patent [19]

Fernandez et al.

[11] Patent Number: 4,557,257

[45] Date of Patent: Dec. 10, 1985

[54] PNEUMATIC WALKING BRACE AND OPERATING SYSTEM

[76] Inventors: José M. Fernandez, P.O. Box 7383, Pampanos Station, Ponce, P.R. 00732; Bulcourt Carlos J., 8600 Twin Lake Dr., Boca Raton, Fla. 33434

[21] Appl. No.: 515,598

[22] Filed: Jul. 21, 1983

[51] Int. Cl.⁴ .............................................. A61H 3/04
[52] U.S. Cl. ............................... 128/80 G; 128/80 F; 128/83.5; 623/26
[58] Field of Search ................... 128/80 G, 25 R, 83.5, 128/68.1, 80 R, 80 F; 3/1.2, 1

[56] References Cited

U.S. PATENT DOCUMENTS

| | | | |
|---|---|---|---|
| 2,111,018 | 3/1938 | Ahler | 3/1.2 |
| 2,573,866 | 11/1951 | Murphy | 128/80 F |
| 3,221,769 | 12/1965 | Kiessling | 3/1.2 |
| 4,180,870 | 1/1980 | Radulovic et al. | 3/1.2 |
| 4,290,423 | 9/1981 | Kleinwolterink | 128/80 G |

*Primary Examiner*—C. Fred Rosenbaum
*Assistant Examiner*—Mario Costantino
*Attorney, Agent, or Firm*—Scrivener Clarke Scrivener and Johnson

[57] ABSTRACT

An apparatus and operating system to be used by a paraplegic or other crippled person has a patient-supporting walker of stable construction, braces extending entirely along the user's legs, a body-supported pneumatic system for alternately moving the legs in a predetermined manner, and user-operated control means for operating the system.

7 Claims, 7 Drawing Figures

PNEUMATIC WALKING BRACE AND OPERATING SYSTEM

SUMMARY OF THE INVENTION

An apparatus worn by a paraplegic or other crippled person has an elongated brace which extends along the outside of each leg and is pivoted at its upper end to a belt at the hip joint level. A double-acting cylinder and piston supported by the belt is provided for each leg and the piston for one leg is operated to first advance that leg about the pivot to a forwardly inclined position, then the piston is operated in the reverse direction to bring the body to erect position about the pivot of the advanced leg, then the operation is repeated with the other leg, and this is continued to produce a walking motion. A four-legged wheeled walker provides support to the user of the apparatus and carries a source of compressed air and user-operated valves which control the supply of air to the cylinders to move the legs in the designed sequence.

BACKGROUND OF THE INVENTION

Modern concepts in rehabilitation medicine emphasize the need for programs of improvement in muscle, nerve and bone tone, which can only be achieved by a program requiring movement of the patient, preferably by walking. However, physicians, physiotherapists and other professional and non-professional persons who work with paraplegics and other crippled persons have found disappointing results in their efforts to improve the patient's condition by a program of supported walking. This has been due, at least in part, to the great amount of physical energy which the patient must expend, with consequent cardiovascular and respiratory stress. These adverse effects, together with unacceptable fatigue, are such that the ratio of patient' acceptance of the programs and continued compliance with it are very low, and it is usually found that the patient gives up the program and reverts to the use of a wheelchair.

It has therefore been a principal object of our invention to provide means by which a patient is given a walking movement, assisted by means which produce the beneficial results of walking and at the same time eliminating the fatigue and the adverse cardiovascular and respiratory effects which have made known walking programs ineffective and unacceptable to the patients. This object has been achieved by the apparatus and system provided by this invention.

DESCRIPTION OF THE PREFERRED EMBODIMENT OF THE INVENTION

The preferred form of the apparatus and operating system provided by our invention for producing a walking motion by a user such as a paraplegic comprises, first, a stable wheeled device, known as a walker, which is grasped by an erect patient wearing the apparatus provided by the invention and is advanced by him/her in forward motion, a pivotally supported vertical brace iron extending along the outside of each leg, two body-carried pneumatic devices for alternately operating the leg braces in a designed sequence of movements, a source of compressed air carried by the walker, and a control system operable by the user for supplying compressed air from the source to the brace operating means for causing the user to perform a forward walking movement.

Figure 1:
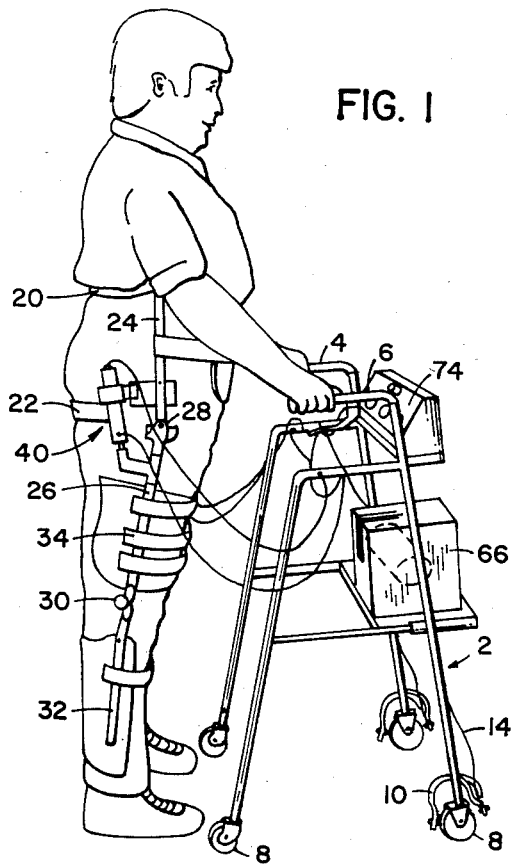
FIG. 1 is a perspective view of a paraplegic with the apparatus provided by the invention.

The walker which forms part of the apparatus provided by the invention is shown at 2 in the drawings and, as stated, is a stable structure having four legs, suitably braced, and having at its upper end longitudinally extending handles 4, 6 the height of the walker being such that the handles may be grasped by the hands of the user when in an erect position, as shown in FIG. 1 of the drawings. Each of the four legs of the walker has a wheel 8 mounted on its lower end, and brakes 10 are positioned adjacent at least the two forward wheels and are operated by handles 12 each of which is pivotally mounted on one of the handles and is connected through an operating wire 14 to the brake below it.

The brace means carried by the user of the invention comprises, first, a belt or similar support 20 surrounding the body at the waist, and a second belt or similar support 22 surrounding the body at the hip joint level. These two belts are connected at each side of the body by a substantially vertical rigid rod 24, the lower end of which is positioned below the lower belt 22 at the hip joint level. A second vertical rod 26 formed of strong rigid material is pivotally connected at its upper end by pivot 28 to the lower end of the rod 24, and extends from the pivot downwardly to the knee where it is pivotally connected at 30 to the upper end of a vertical rod 32 which extends downwardly to the foot where it may be connected to, or received within, the shoe of the user. Suitable wrappings 34 may surround each leg above and below the knee to provide secure attachment of the upper and lower brace parts 26, 32.

Figure 2:
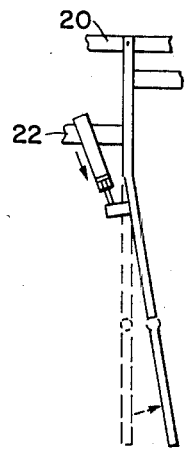
FIGS. 2 and 3 illustrate the apparatus schematically, showing successive steps in the movement of each leg in the operation of the system provided by the invention.
Figure 3:
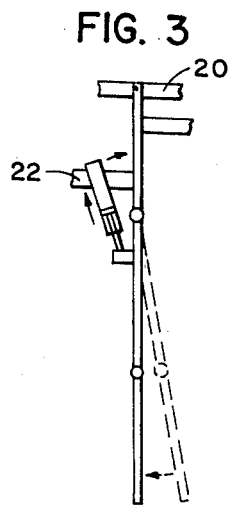

Means are provided by the invention which, when supplied with compressed air will cause alternate forward movement of the legs in a controlled, designed sequence and mode of forward advancement. Such means are illustrated in FIGS. 1 to 3 and, more particularly, in FIG. 4 and comprise, first two pneumatically operated cylinder and piston devices 40, 40a, one for each leg. These two devices and their supporting means are identical and only one will be described. The cylinder 42 is positioned substantially vertically and is pivotally supported approximately midway its length between the spaced parallel arms 44, 46 of a U-shaped bracket 48 the cross member of which is connected to the lower belt 22. Piston rod 50 protrudes downwardly from the lower end of the cylinder, and at its lower end is pivotally connected by pin 52 to the outer end of a short rod 54 the other end of which is adjustably connected, as by hose clamps 55 to the upper brace rod 26.

Figure 6:
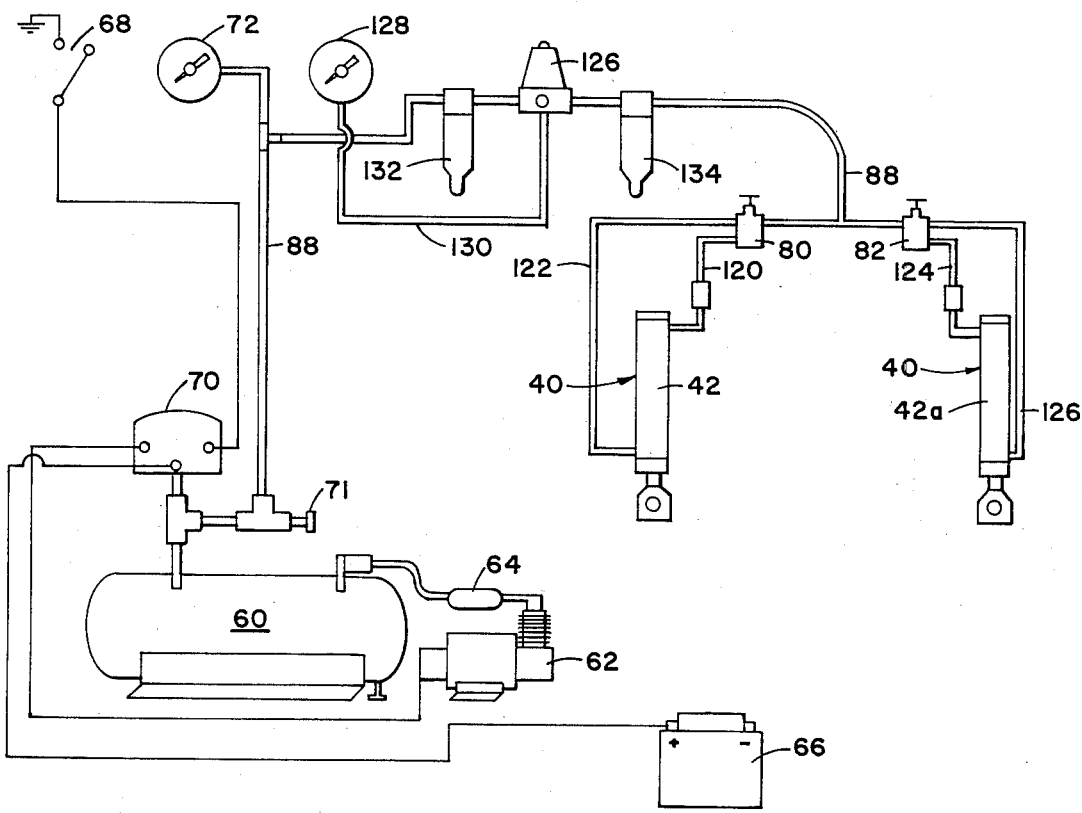
FIG. 6 is a diagram of the system provided by the invention.
Figure 5:
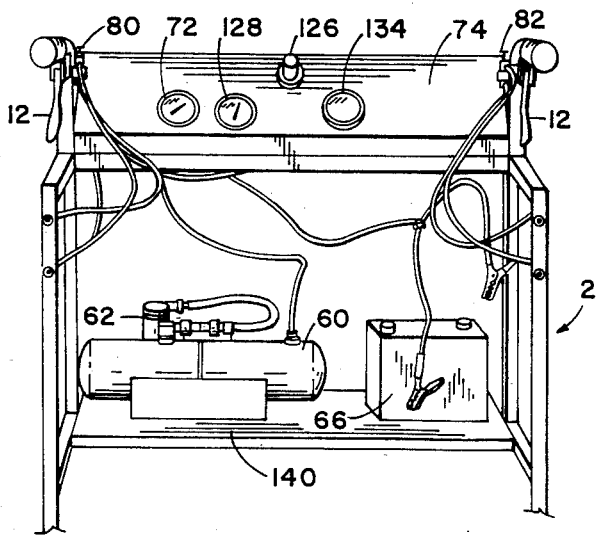
FIG. 5 is a view showing the walker and its associated parts.

Means are provided by the invention which are under the control of the user and which are operable to effect alternate forward movement of the legs in a controlled manner which is in accordance with the movement of the body in normal, un-assisted walking. Such means comprises a pneumatic system for supplying compressed air to the operating cylinders 42, 42a and is disclosed in FIG. 6. The apparatus is mounted on the walker, and comprises a compressed air tank 60 and an electrically operated pump 62 for supplying compressed air to the tank through suitable tubing which includes a check valve 64. A 12-volt electrical circuit including a battery 66, switch 68 and suitable wiring is provided for operating the pump under control of the user. A pressure switch 70 is also provided for effecting automatic charging of the pressure tank when the air in the tank falls below a pre-determined pressure, and a safety valve 71 is provided for relieving excess tank pressure. Suitable tubing leads from the tank to a pressure gauge 72 on the console panel 74 of the walker.

Figure 7:
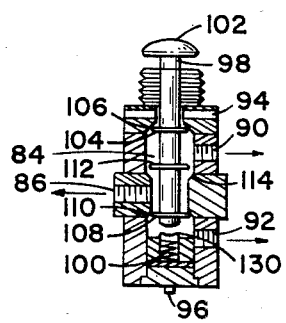
FIG. 7 is a longitudinal sectional view of one of the two operating valves.

Means are provided by the invention for controlling the supply of compressed air from the tank 60 to the cylinders 42, 42a in a designed sequence to produce a walking movement of the legs of the user through the intermediary of the leg braces. Such means comprise two user-operated valves 80, 82 which are mounted on the walker console adjacent, respectively, the handles 4, 6 and therefore in position to be operated by the thumbs of the user as his hands grasp the handles. The two valves are identical and, as shown in FIG. 7, each comprises a cylindrical casing having a central interior chamber 84. An inlet port 86 is provided centrally of the length of the interior chamber and is connected by tubing 88 to the compressed air tank. Power ports 90, 92 open into the central chamber above and below the inlet port, and exhaust ports 94, 96 open into the upper and lower ends of the central chamber, respectively. A valve stem 98 extends axially through the central chamber of the valve and is urged upwardly by a spring 100 so that its head 102 protrudes above the valve casing giving ready access to the thumb or fingers of the user. A valve 104 mounted on the upper part of the valve stem co-operates with a valve seat 106 to control connection of the upper exhaust port 94 and the upper power port 90. A second valve 108 mounted on the lower part of the valve stem co-operates with a valve seat 110 to control connection of the lower exhaust port 96 and the lower power port 92 and also control connection of the inlet port 86 to the power port 92. A third valve 112 is mounted on the valve stem between valves 104, 108 and co-operates with a valve seat 114 to control connection of inlet port 86 with power ports 90 and 92. The power ports 90, 92 of valve 80, which controls the left leg, are connected by tubing 120, 122 to cylinder 42 above and below the piston, and the power ports 90, 92 of valve 82, which controls the right leg, are connected by tubing 124, 126 to cylinder 42a above and below the piston.

The construction of each valve and its connection to a cylinder is such that in its normal un-depressed condition valves 104 and 108 engage their valve seats and valve 112 is off of its seat, thus supplying compressed air through inlet port 86, the open valve 112, 114 and power port 90 to both cylinders 42 and 42a below the piston, thus maintaining both pistons in retracted position. At the same time lower valve 108, 110 is closed, connected power port 92 to exhaust port 96 through the upper end of the exhaust port which is open when the valve stem is in raised, inoperative position as shown at 130 in FIG. 7, thereby exhausting each cylinder above the piston. On depression of the valve stem the upper valve 104, 106 opens, connecting power port 90 to atmosphere through exhaust port 94 and thereby relieving the pressure below the piston. Valve 112, 114 is closed by this movement of the valve stem, thereby disconnecting power port 90 from the inlet port 86 and connecting the inlet port to power port 92 and the cylinder above the piston, at the same time closing the exhaust port 96 and connecting the inlet port 86 to power port 92 and the cylinder above the piston to force the piston down.

OPERATION

Figure 4:
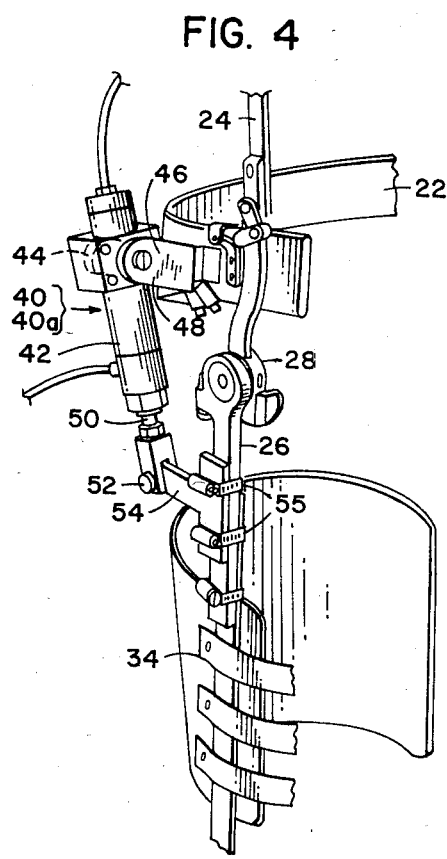
FIG. 4 is a perspective view of the operating apparatus provided for each leg.

The use and operation of the system will now be described, and reference will be made to FIGS. 2, 3 and 4 to illustrate the bodily movements that take place as the system is operated. In FIG. 1 the user is shown erect, grasping the side handles of the walker, and preparing to operate the system to advance his right leg as the first step in a walking program. The operating button 102 of both valves 80, 82 is now up and in its inoperative position, as shown in FIG. 7, the piston in both cylinders is held in its up, or retracted, position by compressed air supplied to the cylinder below the piston through valve inlet port 86, open valve 112, 114, valve chamber 90 and power port 90. The user now wishes to advance his right leg, and therefore depresses the valve stem of valve 82 by pushing on button 102, thereby connecting the lower end of the cylinder 42a to atmosphere through valve port 90, opened valve 104, 106 and exhaust port 94. At the same time compressed air is supplied to the cylinder above the piston from valve inlet port 86, the central valve chamber, opened valve 108, 110 and power port 92. The piston is thereby moved downwardly, forcing the short rod 54 in a counterclockwise direction and carrying with it the brace 26, 32 which is pivotally supported at its upper end at the hip joint level of the user. The valve operating button is maintained depressed until the piston completes its stroke, and when this occurs the right leg is in an inclined position extending forwardly from the pivot at the upper end of brace rod 26, as shown in FIG. 2.

This completes the forward movement of the right leg, and the forward movement of the body is now completed by bringing the body to erect position using the foot of the forwardly inclined right leg as a pivot. This movement is effected by releasing the valve operating button 102, causing the valve stem to be moved upwardly by spring 100 to its normal condition, causing the cylinder above the piston to be connected to atmosphere and the cylinder below the piston to be connected to the source of compressed air through the valve and ports described above. The piston is therefore moved upwardly, moving the short rod 54 and the attached leg brace 26, 32 in a clockwise direction about a pivot provided by the foot of the right leg, thus moving the upper end of brace rod 26, 32 and the upper and lower belts 20, 22 also in a clockwise direction to bring the body to an erect position as the right leg and its attached brace reaches and assumes a vertical position, as shown in FIG. 3.

This completes the forward step of the right leg, and the left leg control is now operated by depressing the operating button of the left leg control valve 80 to operate the left leg operating means and initiate and complete the same cycle of operations which is described above for operation of the right leg. Thus, the user may perform a walking program of any desired distance or duration of time by alternately depressing, holding and releasing the button operators of the valves for the left and right cylinder and piston leg operators.

Means are provided by the invention for varying the length of the steps, which is accomplished by varying the cylinder pressure under control of the user, and such means comprise the knob-operated pressure regulator valve 126 and the cylinder pressure gauge 128, which is connected by tubing 130 to the valve 126, and both of which are mounted on this console. By reading the cylinder pressure on the gauge 128 and adjusting it by operation of valve 126 the user may, by adjusting cylinder pressure, vary the length of all steps produced by operation of the system until the regulator valve is further adjusted.

On the upstream side of cylinder pressure regulator valve 126, in tubing 88, there is a device 132 for collecting humidity in the air system before reaching the cylinder pressure regulator valve 126, and on the downstream side of that valve in tubing 88 there is a device 134 for introducing lubricating oil into the tubing leading to the operating valves 80, 82 and the operating cylinders.

The provision of a pneumatic operating system, with a reservoir of compressed air, insures against breakdown of the system due to lack of power, which is a disadvantage of a hydraulically operated walking system. Operation at all times is further insured by the provision of a walker carried air compressor pump which is electrically operated by a walker-carried battery, thereby further insuring the system against failure and making it self-contained without the necessity of plugging into a source of electrical energy during the walking time.

We claim:

1. A walking system for assisting a person to stand in an upright position and for alternately moving the legs to cause a walking movement, comprising:
   (a) a wheeled walker of a height permitting its upper part to be grasped by the hands of an erect user of the system,
   (b) a normally vertical leg brace extending along the outside of each leg which is pivotally supported at its upper end in relation to the body at the level of the hip joint, and is connected to the leg below the knee joint,
   (c) pneumatically operated means for moving the brace of each of the legs in a counter-clockwise direction about the pivotal support at its upper end from its normal vertical position to a position inclined forwardly from that support, and
   (d) pneumatically operated means for then moving the brace of the same leg in a clockwise direction about the pivotal support at its upper end from the forwardly inclined position to a vertical position.

2. The walking system according to claim 1, comprising in addition a belt encircling the waist of the user, a second belt encircling the user at the level of the hip joint, and rigid means connecting the belts, each leg brace being pivotally connected to the means connecting the two belts.

3. The walking system according to claim 2, in which each of the pneumatic means comprises a cylinder and piston assembly vertically mounted on the means connecting the two belts, and means connecting each piston to a brace below the pivotal connection of the brace to the means connecting the two belts.

4. The walking system according to claim 1, comprising in addition, a pneumatic system including the pneumatically operated means, a source of compressed air, user operable valve means for supplying compressed air from the source to the pneumatically operated means in sequence to cause the said movements of the brace, and tubing connecting the source of compressed air to the valves and pistons.

5. The walking system according to claim 4, in which the source of compressed air and the valve means are mounted on the walker with the valve means positioned for easy access by the hands of the user.

6. A walking system for assisting a person to stand in an upright position and for alternately moving the legs to cause a walking movement, comprising:
   (a) a wheeled walker of a height permitting its upper part to be grasped by the hands of an erect user of the system,
   (b) a normally vertical leg brace extending along the outside of each leg which is pivotally supported at its upper end in relation to the body at the level of the hip joint, and the lower part of which is connected to the leg below the knee joint,
   (c) a double acting pneumatic cylinder connected to each side of the body of the user and having a piston connected to the adjacent brace below the pivotal support of the upper end of the brace,
   (d) a source of compressed air,
   (e) control valves positioned on the walker to be operated by the user, and connections between the control valves, the source of compressed air and the cylinder to cause upon operation of the control valves:
      i. operation of a piston to move the connected brace and its attached leg in the counter-clockwise direction about the pivot at the upper end of the brace to a forwardly inclined position, and subsequent
      ii. operation of the same piston to move the brace and its attached leg in the clockwise direction about the pivot point to the upright position.

7. A walking system for assisting a person to stand in an upright position and for alternately moving the legs to cause a walking movement, comprising:
   (a) a wheeled walker of a height permitting its upper part to be grasped by the hands of an erect user of the apparatus, and
   (b) a body harness comprising a belt encircling the body of the user at waist level, a second belt encircling the body at the hip joint level, and rigid means connecting the belts at each side of the body,
   (c) a normally vertical leg brace extending along the outside of each leg which is pivoted at its upper end in relation to the body at the level of the hip joint, and which is connected to the leg below the knee joint,
   (d) two pneumatically operated cylinder and piston means each of which is mounted on one side of the body on the second belt, and adjacent the upper end of a brace,
   (e) a connection between each piston and the adjacent brace below the pivotal support of the upper end of the brace, and
   (f) means for alternately operating the pneumatic means of the two legs to cause each piston to
      i. first move the connected brace and its attached leg in counter-clockwise direction about the pivotal support of the upper end of the brace to a forwardly inclined position, and
      ii. then to move the same brace and its attached leg in the clockwise direction about the pivotal support of the upper end of the brace to an upright position.

* * * * *